United States Patent [19]

Harris

[11] 4,275,247

[45] Jun. 23, 1981

[54] PROCESS FOR PREPARING AN ORGANIC COMPOUND

[75] Inventor: John F. Harris, Royston, England

[73] Assignee: Fisons Limited, London, England

[21] Appl. No.: 107,615

[22] Filed: Dec. 27, 1979

[30] Foreign Application Priority Data

Dec. 27, 1978 [GB] United Kingdom ............... 49996/78

[51] Int. Cl.$^3$ ............................................ C07C 37/06
[52] U.S. Cl. ................................................... 568/767
[58] Field of Search ................................. 568/763, 767

[56] References Cited

PUBLICATIONS

Manok, Ferene et al., *Monatshefte fur Chemie*, vol. 109, pp. 1329-1326, (1978).

Pines, Seemon H. et al., *J. Org. Chem.*, vol. 31, pp. 3446-3447, (1966).

Kliegman, Jonathan M. et al., *J. Org. Chem.*, vol. 37, pp. 4223-4224, (1972).

Pecherer, B. et al., *J. Am. Chem. Soc.*, vol. 70, pp. 2587-2589, (1948).

*Primary Examiner*—Robert Gerstl
*Assistant Examiner*—L. Hendriksen
*Attorney, Agent, or Firm*—Wenderoth, Lind & Ponack

[57] ABSTRACT

Pyrogallol or a salt thereof is prepared by a process comprising deoximating cyclohexane-1,2,3-trione oxime or an oxime derivative thereof or a salt of either. Preferably the oxime itself is exployed, especially the 1,3-dioxime. The deoximation is preferably effected by hydrolysis.

25 Claims, No Drawings

PROCESS FOR PREPARING AN ORGANIC COMPOUND

This invention relates to a process for preparing pyrogallol, 1,2,3-trihydroxybenzene.

Pyrogallol has various uses, for instance as a photographic developer, in dyeing leather and wool, in the analysis of heavy metals and as an intermediate e.g. in the production of the pesticide 2,2-dimethyl-1,3-benzodioxol-4-yl methylcarbamate. At present, all the pyrogallol available in commerce is prepared by decarboxylation of gallic acid obtained from comparatively rare plant sources. This makes pyrogallol expensive and difficult to procure. We have now discovered a much improved process for its preparation, which avoids such rare plant sources and produces pyrogallol readily.

Accordingly, the invention provides a process for preparing pyrogallol or a salt thereof, which process comprises deoximating cyclohexane-1,2,3-trione oxime or an oxime derivative thereof or a salt of either.

The process is simple and employs a readily made starting material. The starting material can be prepared for instance from cyclohexanone or cyclohexane, which are relatively cheap bulk commodities. The starting material can be prepared in known ways. Cyclohexane-1,2,3-trione 1,3-dioxime can be prepared, for instance, by reacting cyclohexanone with nitrous acid (e.g. formed in situ by reaction of acetic acid and sodium nitrite). Cyclohexane can be reacted, e.g. with nitrosyl chloride, to form cyclohexanone oxime, and this may be converted to cyclohexane-1,2,3-trione 1,2,3-trioxime e.g. by nitrosyl chloride or nitrous acid.

Deoximation is the conversion of an oxime to the corresponding carbonyl compound and is a procedure known in itself (see for instance Synthesis, 1976, page 610). It may be carried out for example by:

(a) Oxime Exchange. This is the exchange of an oxime group >C=NOH with a carbonyl group >C=O, for example using a ketone e.g. acetone, see for instance Maynez S R, Pelavin L and Erker G, J Org Chem, volume 40, the article begining on page 3302.

(b) Nucleophilic addition to the oxime group, followed by hydrolysis. It may be carried out for example by (i) bisulphite ion (e.g. provided by sodium or calcium bisulphite) in the presence of water, usually followed by acid hydrolysis, see for instance Pines S H, Chemerda J M and Kozlowski M A, J Org Chem, volume 31, the article beginning on page 3446; or (ii) formaldehyde and acid, usually mineral acid e.g. hydrochloric acid, see for instance Cava M P, Little R L and Napier D R, J Amer Chem Soc, volume 80, the article beginning on page 2257.

(c) Reductive Deoximation, for example by chromous acetate or titanium trichloride, e.g. in aqueous tetrahydrofuran solution, see for instance (i) Pappo R, Garland R B, Jung C J and Nicholson R T, Tetrahedron Letters, 1973, the article beginning on page 1827; (ii) Corey E J and Richman J E, J Amer Chem Soc, volume 92, the article beginning on page 5276; and (iii) Timms G H and Wildsmith E, Tetrahedron Letters, 1971, the article beginning on page 195.

(d) Oxidative Deoximation, for example by (i) thallium (III) nitrate, e.g. in methanol, see for instance McKillop A, Hunt J D, Naylor R D and Taylor E C, J Amer Chem Soc, volume 93, the article beginning on page 4918, (ii) alkali (e.g. sodium) hypochlorite, see for instance Ho T L and Wong C M, J Org Chem, volume 39, the article beginning at page 3453, or (iii) nitrous acid (e.g. provided by sodium nitrite and acid e.g. acetic acid) in the presence of water, see for instance Kliegman J M and Barnes R K, J Org Chem, volume 37, the article beginning on page 4223.

(e) Hydrolysis. This is reaction with water, see for instance (i) Hartman W W and Roll L J, Organic Syn Coll, volume III, the article beginning on page 20; (ii) Hershberg E B, J Org Chem, volume 13, the article beginning on page 542; and (iii) DePuy C H and Ponder B W, J Amer Chem Soc, volume 81, the article beginning on page 4629.

This is not a rigid classification, as is shown by the articles referred to above. For instance, the use of formaldehyde and acid can be regarded as oxime exchange (a), hydrolysis (e), or nucleophilic addition followed by hydrolysis (b). A particular deoximation may involve elements of more than one of these classes.

We have found surprisingly that pyrogallol can readily be produced by subjecting cyclohexane-1,2,3-trione oxime or an oxime derivative thereof or a salt of either to deoximation conditions.

Pyrogallol forms salts by reason of its phenolic OH groups. The salts include particularly alkali metal, e.g. sodium or potassium, especially sodium, salts and can be prepared in conventional ways from pyrogallol, e.g. by reaction with alkali metal alkoxides. Pyrogallol itself can be prepared from its salts in conventional ways e.g. by reaction with acid for example hydrochloric acid. Usually pyrogallol itself is formed in the process of the invention, but it can be converted to a salt if desired though this is not preferred.

The starting material is preferably supplied to the deoximation conditions as the oxime itself. It may, however, be supplied as an oxime derivative of the oxime, usually an ester (which may be formed from the oxime itself by esterification e.g. acetylation). The ester is usually an ester of the oxime with benzoic acid or an alkanoic acid of 2-7 carbon atoms particularly acetic acid. The ester may be for example the diacetyl or dibenzoyl ester of the 1,3-dioxime. The starting material may be supplied as a salt of the oxime or of a derivative of the oxime. Salts which may be employed include the sodium, potassium and ammonium salts. If one starts with a salt or derivative, this is generally converted under the deoximation conditions to the oxime, which is then deoximated.

The oxime may be monoxime, dioxime or trioxime. It may be for example the 2-monoxime or the 1,2,3-trioxime. Preferably, however, the oxime is cyclohexane-1,2,3-trione 1,3-dioxime.

The present process is usually carried out in a solvent, generally water. It is usually conducted at a temperature above −15° C., preferably above −5° C., especially above 20° C. The temperature is usually below 200° C., preferably below 140° C., especially below 120° C.

The deoximation may be carried out in various ways, for instance the ways referred to above. For example, it can be brought about by a process comprising reacting the oxime, derivative or salt with bisulphite ion (e.g. provided by sodium or calcium bisulphite) in the presence of water, usually at a temperature from 20° to 140° C. It can be brought about by a process comprising reacting the oxime, derivative or salt with nitrous acid (e.g. provided by a nitrite, usually sodium nitrite, and acid, e.g. hydrochoric acid) in the presence of water, usually at a temperature from −15° to 30° C., preferably from 0° to 10° C.

Preferably, the deoximation is carried out by a process comprising hydrolysing the oxime, derivative or salt.

The hydrolysis is usually carried out under acidic conditions, i.e. at a pH below 7. Generally the pH is up to 6, preferably up to 5, especially up to 4.5. Generally the pH is above −1, preferably above 0, especially above 1. The acid employed to achieve the acid conditions may be a mineral acid, e.g. hydrochloric acid, or preferably, an organic acid for example an aromatic acid such as phthalic acid, benzoic acid, o-nitrobenzoic acid, 2,4-dichlorophenol or p-toluenesulphonic acid or a weak aliphatic acid such as oxalic acid or acetic acid.

The hydrolysis can be conducted in the presence of an aldehyde or ketone, for example acetone or isobutyl methyl ketone. In that aspect, some element of exchange of oxime group from the cyclohexane-1,2,3-trione oxime with the carbonyl group of the aldehyde or ketone may occur, or the ketone may react with hydroxylamine produced in the hydrolysis.

The carbonyl and acid functions can be provided in the same compound, i.e. an aldehyde-acid or a keto-acid, for instance pyruvic acid, levulinic acid or glyoxylic acid, preferably pyruvic acid.

A mixture of acids can be employed.

The pH is preferably maintained within the above limits throughout the hydrolysis. This can be done by adding further acid as the hydrolysis proceeds. The pH can be buffered. This can be achieved by a salt of an organic base. The salt can be supplied as such, or as equivalent amounts of its base and acid separately; either way, the hydrolysis is regarded as being conducted in the presence of the acid and base. The acid can be, for instance, hydrochloric acid or a dicarboxylic acid such as oxalic acid, adipic acid or citric acid. The base can be, for instance, an organic base such as a secondary or tertiary amine, e.g. pyridine, N-methylaniline, N,N-dimethylaniline, morpholine, diphenylamine, diisopropylamine, dimethylamine or triethanolamine. Thus, the hydrolysis can be conductd, for example, at a pH of from −1 to 6 in the presence of a secondary or tertiary amine, the acid required to produce this pH being, for instance, a mixture of an aldehyde- or keto-acid and the acid, such as hydrochloric acid, equivalent to the amine to provide the buffer.

The amount of water employed in the hydrolysis is usually 0.2-1000, preferably 0.2-500, especially 0.2-100, e.g. 2-20, parts by weight per part by weight of the oxime, its derivative or salt of either.

The hydrolysis is conveniently conducted in the presence of an inert solvent, e.g. excess water over that required in the hydrolysis. Co-solvents may be employed, e.g. acetone, isobutyl methyl ketone or acetic acid. As explained above, these may act as more than just co-solvents.

A phase transfer catalyst, for instance a quaternary ammonium phase transfer catalyst, e.g. Adogen 464, can be employed in the hydrolysis.

The hydrolysis may be conducted at a temperature for example from 20° to 140° C., e.g. from 20° to 120° C. The reaction mixture is usually heated. The temperature may be for instance 40°-140°0 C., preferably 40°-120° C.

A combination of different classes of deoximation techniques may be employed, e.g. by reacting with bisulphite ion in the presence of water and an aldehydoacid or keto-acid, e.g. pyruvic acid.

The present process may be conducted under a pressure which is above, at, or below atmospheric pressure. The pressure may be for instance 0.1-15 atmospheres, conveniently atmospheric pressure.

The deoximation generally produces pyrogallol directly. Where only cyclohexane-1,2,3-trione results, this can readily be converted to pyrogallol, e.g. by heating with acid, e.g. at a pH from −1 to 6, for example using an acid referred to above, or with toluene.

Pyrogallol and its salts absorb oxygen when hot, and the salts absorb oxygen even at ambient temperature. Accordingly, excessive heating of them should be avoided, and it may be desirable in some instances to produce the pyrogallol or salt thereof in an inert atmosphere, e.g. an atmosphere of nitrogen or carbon dioxide.

The present product can be extracted and purified in conventional ways.

The pyrogallol is particularly suitable for reaction with 2,2-dimethoxypropane to form 2,2-dimethyl-4-hydroxy-1,3-benzodioxole, and then reaction of this with methyl isocyanate to produce the pesticide 2,2-dimethyl-1,3-benzodioxol-4-yl methylcarbamate.

The invention is illustrated by the following Examples, in which parts and percentages are by weight and dioxide means cyclohexane-1,2,3-trione 1,3-dioxime.

EXAMPLE 1

Cyclohexane-1,2,3-trione 1,3-dioxime was prepared by a modification of the method of Treibs and Kuhn (Ber 90, 1691-6, 1957) in that cyclohexanone (100 parts), sodium nitrite (214 parts), ethanol (242 parts), $H_2O$ (272 parts) and glacial acetic acid (321 parts) were mixed and stood for nine days, the mixture filtered and the solid slurried in water, then concentrated hydrochloric acid solution (261 parts) added and the yellow cyclohexane-1,2,3-trione-1,3-dioxime filtered off and dried in air (69 parts, 43% yield).

EXAMPLE 2

To cyclohexane-1,2,3-trione 1,3-dioxime (100 parts) were added glacial acetic acid (400 parts) and water (1600 parts) and the mixture refluxed for four hours at 100°-100.5° C. The pyrogallol was extracted and purified as follows. 47.3% NaOH solution (483 parts) was added to the cooled mixture, when the pH rose from 3.4 to 6.0. The mixture was filtered giving insolubles (60 parts), and the filtrate was continuously extracted with ether. The extract was dried over $Na_2SO_4$ and evaporated. The residue was triturated with water and the mixture filtered giving insolubles (8 parts) and a filtrate which was evaporated on a water bath to give a tar (8 parts). To this tar were added glacial acetic acid (42 parts) and acetic anhydride (70 parts) and a catalytic amount of pyridine. After standing at room temperature for five hours, the mixture was drowned out in water and the tar obtained recrystallised from methanol (8 parts) to give pyrogallol triacetate (1 part), melting point 161°-163° C., (0.5% yield).

To 100 parts of pyrogallol triacetate as prepared above were added glacial acetic acid (364 parts) and 2 N HCl solution (3640 parts) and the mixture refluxed for three hours under a nitrogen blanket. Continuous ether extraction followed by evaporation of the extract gave an oil which slowly crystallised. Recrystallisation from toluene gave pyrogallol (44 parts, 87% yield).

EXAMPLE 3

| | | |
|---|---|---|
| Dioxime | | 2.5 g |
| Water | | 250 ml |
| Pyruvic acid | 4.25 g | } mixed together |
| Glacial acetic acid | 12.5 ml | |

The dioxime and water were heated to reflux to give a solution of pH 5. The pH was adjusted to 3.9 by adding some of the mixture of pyruvic acid and acetic acid. While continuing to heat the reaction mixture under reflux, the pH was kept in the range 4–4.5 by the addition of more of the mixture of pyruvic acid and acetic acid. The total reaction time was 25 hours. The total amount of pyruvic acid and acetic acid employed was 3.53 g (20% of the mixture prepared). Thin layer chromatography (TLC) showed the product to contain pyrogallol.

EXAMPLES 4–8

2.5 G of dioxime, 50 ml of water and the amounts of the amine hydrochlorides named (added as a mixture of the amine and the corresponding weight of HCL) in the table below were heated under reflux for the times shown. The reaction mixture went brown or black. TLC showed that pyrogallol was formed, $\checkmark$ indicating a little and $\checkmark\checkmark$ much.

| Amine Hydrochloride | Time, hours | Pyrogallol |
|---|---|---|
| Pyridine hydrochloride 25g | 16.5 | $\checkmark$ |
| N,N-dimethylaniline 5.8g + concentrated HCl 3.3 ml | 4 | $\checkmark\checkmark$ |
| Morpholine 4.2g + concentrated HCl 3.3 ml | 7 | $\checkmark\checkmark$ |
| Pyridine 3.9 ml + concentrated HCL 3.3 ml | 22 | $\checkmark\checkmark$ |
| Triethanolamine 7.1g + concentrated HCL 3.3 ml | 22 | $\checkmark$ |

EXAMPLE 9

Dioxime (2.5 g), water (50 ml) and phthalic acid (3.2 g) were heated under reflux for 4–16 hours. The mixture turned brown. TLC showed that a little pyrogallol was found.

EXAMPLE 10

N,N-dimethylaniline (5.8 g), water (25 ml), isobutyl methyl ketone (25 ml) and concentrated hydrochloric acid (3.3 ml) were heated under reflux for 4 hours. TLC showed that much pyrogallol was formed.

EXAMPLE 11

| | |
|---|---|
| Dioxime | 2.5g |
| Pyruvic Acid | 4.25g |
| Glacial acetic acid | 12.5 ml |
| Water | 25 ml |

These amounts of these reactants were heated under reflux for 2 hours 25 minutes. The reaction product was cooled, neutralised with sodium hydroxide or sodium bicarbonate and then continuously extracted with ether. Evaporation yielded 0.76 g of black oil. Analysis gave 41.7% pyrogallol, equivalent to a yield of 15.7%.

EXAMPLE 12

Example 11 was repeated except that 0.5 ml instead of 25 ml of water was employed. The reflux temperature was 112° C. Pyrogallol (0.5% yield) was obtained.

EXAMPLES 13 AND 14

Example 11 was repeated except that 250 ml and 1250 ml instead of 25 ml of water was employed. The yield of pyrogallol was 28% and 26% respectively.

EXAMPLE 15

Example 11 was repeated except that the reactants were heated at 40° C. for 5 days. The yield of pyrogallol was 9.4%.

EXAMPLE 16

Example 11 was repeated except that the reactants were not heated (the temperature thus remained ambient, 20° C.) and the reaction mixture was neutralised after 14 days. The yield of pyrogallol was 13.7%.

EXAMPLE 17

Dioxime (2 parts), pyruvic acid (6.9 parts), glacial acetic acid (21.2 parts) and water (40.5 parts) were heated under reflux for 1½ hours, cooled and neutralised with solid sodium bicarbonate. The product was then continuously extracted with diethyl ether, and the ether then evaporated off to yield a black oil (0.54 parts) containing 41.0% pyrogallol. The yield of pyrogallol was 13.7%.

EXAMPLE 18

Dioxime (2.5 g), acetone (25 ml), water (25 ml) and p-toluene-sulphonic acid (7.3 g) were heated under reflux for 3 hours. The reflux temperature was 69° C. The mixture was then cooled and continuously extracted with ether to yield 1.2 g of product containing 4.3% pyrogallol, equivalent to a yield of 2.6%.

EXAMPLE 19

Dioxime (2.5 g), acetone (20 ml), water (20 ml) and phthalic acid (10 g) were heated under reflux, at a temperature of 73° C., for 4 hours 20 minutes. The mixture was cooled and then continuously extracted with ether. The ether extract was dried over $MgSO_4$. Evaporation then yielded 1.2 g of product containing 17.7% pyrogallol, corresponding to a yield of 10.5%.

EXAMPLE 20

Dioxime (2.5 g), isobutyl methyl ketone (25 g), water (25 g) and p-toluenesulphonic acid (0.25 g) were heated under reflux with stirring for 24 hours. The mixture was then cooled, neutralised with sodium bicarbonate and continuously extracted with ether. Evaporation of the ether yielded 1.76 g of black oil containing 7.5% pyrogallol, corresponding to a yield of 6.5%.

EXAMPLES 21–26

Dioxime (2.5 g) was heated under reflux with the amounts of the other materials shown in the table below for the time shown. The mixture was then brown or black. TLC showed that pyrogallol was produced, $\checkmark$ indicating little pyrogallol and $\checkmark\checkmark$ much pyrogallol.

| Materials | Time, hours | Yield of Pyrogallol |
|---|---|---|
| Water (25 ml), acetone (25 ml) + p-toluenesulphonic acid (3.7g) | 1.25 | ✓✓ |
| Water (25 ml), acetone (25 ml) + p-toluenesulphonic acid (7.3g) | 1.25 | ✓✓ |
| Levulinic acid (25g) + water (25g) | 17 | 5.3% |
| Levulinic acid + 1 M hydrochloric acid (9:1 by volume, 75g of mixture) | 1.5 | ✓ |
| Isobutyl methyl ketone (25g), water (25g) + p-toluenesulphonic acid (7.5g) | 17 | ✓ |
| Benzoic acid (3.91g), isobutyl methyl ketone (25g) + water (25g) | 5.25 | ✓ |

EXAMPLE 27

Dioxime (2.5 g) was heated under reflux with water (50 ml) and o-nitrobenzoic acid (10 g) for 5½ hours. The mixture turned black. TLC showed that a small amount of pyrogallol was produced.

EXAMPLE 28

Dioxime (2.5 g) was heated under reflux with isobutyl methyl ketone (25 g), water (25 g), Adogen 464—a phase transfer catalyst (0.25 g)—and p-toluenesulphonic acid (0.25 g) for 6 hours. TLC showed that pyrogallol was produced.

EXAMPLE 29

Dioxime (5 g) and 2 N hydrochloric acid (50 ml) was heated at 75° C. for 15 minutes. Black solid was filtered off. Toluene was added to the filtrate in the proportions of 5 volumes of toluene per volume of filtrate, and heated under reflux via a Dean and Stark head for 2½ hours, by which time all the water had been removed. TLC showed that the resulting tar contained pyrogallol.

EXAMPLE 30

Dioxime (0.25 g) was heated with N hydrochloric acid (5 ml) on a water bath for 30 seconds. TLC showed that the product contained pyrogallol.

EXAMPLE 31

Dioxime (0.25 g) was heated with 0.1 N hydrochloric acid (5 ml) on a water bath for 30 seconds. TLC showed that the product contained pyrogallol.

EXAMPLE 32

Dioxime (0.25 g) was heated with N sulphuric acid (5 ml) on a water bath for 1 hour. TLC showed that the product contained a trace of pyrogallol.

EXAMPLE 33

Dioxime (0.25 g) was heated with 20% acetic acid in water (5 ml) on a water bath for 1 hour. TLC showed that the product contained pyrogallol.

EXAMPLE 34

Dioxime (5 g) and water (100 ml) were heated under reflux while adding N hydrochloric acid dropwise over 2½ hours. The pH dropped gradually from 4.5 to 0. TLC showed that the product contained pyrogallol.

EXAMPLE 35

Following the general procedure of Example 2 except that the initial mixture was heated at 40°-60° C. for 8 days, pyrogallol was produced, which was extracted by conversion to pyrogallol triacetate (0.8 part).

EXAMPLE 36

Dioxime (2.5 g) was heated under reflux with water (50 ml) and 2,4-dichlorophenol (10 g) for 6 hours. TLC showed that the product contained a little pyrogallol.

EXAMPLE 37–41

Dioxime (1 g), water (20 g) and the secondary amine hydrochloride whose amine is specified in the Table below were heated under reflux in an oil bath for the time stated. The hydrochloride was formed from the weight of amine specified and 2.1 ml of concentrated hydrochloric acid (which contributed an additional 1.53 g water to the reaction). The dimethylamine was employed as its 33% solution in ethanol. TLC showed that pyrogallol was produced. The terminal pH was measured, this is quoted in the Table. In those Examples where a yield of pyrogallol is stated, the reaction mixture was diluted with water and continuously extracted with ether, the ethereal solutions were evaporated and the yield was assessed by gas chromatographic analysis of the residue.

| Example | Amine | Amine Weight, g | Reflux Time, hours | Terminal pH | Pyrogallol Yield, % |
|---|---|---|---|---|---|
| 37 | N-methylaniline | 2.74 | 3.2 | 3.6 | 2.6 |
| 38 | Morpholine | 2.23 | 9.2 | 7.9 | 0.4 |
| 39 | Diphenylamine | 4.33 | 3.2 | 0.4 | 3.9 |
| 40 | Diisopropylamine | 2.59 | 8.5 | 6.6 | — |
| 41 | Dimethylamine | 1.15 | 3.0 | 0.8 | 0.9 |

EXAMPLES 42–55

Dioxime (1 g), water (20 g), the secondary or tertiary amine hydrochloride whose amine is specified in the Table below and the keto-acid specified in the Table were heated under reflux (105° C.) in an oil bath for the time stated. The weights of amine used were as follows:

| N-methylaniline | 2.74g |
|---|---|
| Morpholine | 2.23g |
| Diphenylamine | 4.33g |
| Dimethylamine | 1.15g |
| N,N-dimethylaniline | 3.1g |

The dimethylamine was employed as its 33% solution in ethanol in Example 51 and as its 60% solution in water (contributing an additional 0.77 g of water) in Example 52. The hydrochloride was formed from the amine and 2.1 ml of concentrated hydrochloric acid (contributing an additional 1.53 g of water). The weights of acid used were as follows:

| Pyruvic acid | 1.69g |
|---|---|
| Glyoxylic acid | 2.84g of 50% solution in water (contributing an additional 1.42g of water) |
| Levulinic acid | 2.23g |

TLC showed that pyrogallol was produced. The end pH is shown in the Table. The reaction mixture was diluted with water, the pH adjusted to 1, and the mixture continuously extracted with ether. The ether extracts were evaporated to give oils which were analysed for pyrogallol by gas chromatography.

| Example | Amine | Acid | Reflux Time, hours | Terminal pH | Pyrogallol Yield, % |
|---|---|---|---|---|---|
| 42 | N-methylaniline | Pyruvic | 2.1 | 2.2 | 18.3 |
| 43 | " | Glyoxylic | 2.1 | 2.3 | 10.1 |
| 44 | " | Levulinic | 2.1 | 3.2 | 5.0 |
| 45 | Morpholine | Pyruvic | 3 | 3.9 | 13.8 |
| 46 | " | Glyoxylic | 3 | 3.3 | 5.0 |
| 47 | " | Levulinic | 4.5 | 4.2 | 8.3 |
| 48 | Diphenylamine | Pyruvic | 2.1 | 0.2 | 3.5 |
| 49 | " | Glyoxylic | 2.1 | 0.2 | 1.7 |
| 50 | " | Levulinic | 2.1 | 0.5 | 1.3 |
| 51 | Dimethylamine | Pyruvic | 3 | 0.8 | 0.6 |
| 52 | 41 | Levulinic | 3.5 | 1.3 | 1.4 |
| 53 | N,N-dimethylaniline | Pyruvic | 4 | 2.55 | 29.2 |
| 54 | N,N-dimethylaniline | Levulinic | 4 | 3.7 | 6.6 |
| 55 | " | Glyoxylic | 3 | 2.5 | 21.4 |

EXAMPLES 56-84

Dioxime (1 g), water (20 g), the amine specified in the Table below, the keto-acid specified and the dicarboxylic acid specified were heated under reflux in an oil bath for the time stated. The weights of the amine and acids were as follows:
Diphenylamine 4.33 g
N-methylaniline 2.74 g
Morpholine 2.23 g
N,N-dimethylaniline 3.1 g
Pyruvic Acid 1.69 g
Levulinic Acid 2.23 g
Glyoxylic Acid 2.84 g of 50% solution in water (contributing an additional 1.42 g of water)
Oxalic Acid Dihydrate 1.61 g
Adipic Acid 1.87 g
Citric Acid 2.46 g TLC showed that pyrogallol was produced. The end pH is shown in the Table. Where a yield is quoted, the reaction mixture was diluted with water, the pH adjusted to 1 (in Examples 56–69) or 6 (in Examples 70–84), the mixture continuously extracted with ether, and the ether extracts evaporated to give oils which were analysed for pyrogallol by gas chromatography.

| Example | Amine | Keto acid | Dicarboxylic Acid | Reflux Time, hours | Terminal pH | Pyrogallol Yield, % |
|---|---|---|---|---|---|---|
| 56 | diphenylamine | Pyruvic | oxalic | 3½ | 1.1 | 2.1 |
| 57 | " | " | adipic | 3½ | 1.6 | 8.9 |
| 58 | " | " | citric | 3½ | 1.5 | 9.3 |
| 59 | " | glyoxylic | oxalic | 3½ | 1.4 | 0.6 |
| 60 | " | " | adipic | 3½ | 2.8 | 7.6 |
| 61 | " | " | citric | 3½ | 2.2 | 6.6 |
| 62 | " | levulinic | oxalic | 4 | 1.3 | 2.1 |
| 63 | " | " | adipic | 8 | 3.7 | 7.7 |
| 64 | " | " | citric | 4 | 2.7 | 6.4 |
| 65 | N-methylaniline | pyruvic | oxalic | 8 | 3.3 | 14.3 |
| 66 | " | " | adipic | 8 | 4.1 | 6.1 |
| 67 | " | " | citric | 8 | 3.65 | 7.7 |
| 68 | " | glyoxylic | oxalic | 8 | 2.95 | 1.3 |
| 69 | " | " | adipic | 8 | 3.9 | — |
| 70 | " | levulinic | oxalic | 3 | 3.4 | 3.1 |
| 71 | " | " | adipic | 4 | 4.05 | 0.9 |
| 72 | " | " | citric | 4 | 3.7 | 1.4 |
| 73 | morpholine | pyruvic | oxalic | 3 | 3.5 | 16.8 |
| 74 | " | " | adipic | 4 | 4.8 | 6.6 |
| 75 | " | " | citric | 4 | 4.2 | 10.2 |
| 76 | " | glyoxylic | oxalic | 3 | 3.6 | 4.0 |
| 77 | N,N-dimethylaniline | pyruvic | oxalic | 3½ | 3.8 | 26.6 |
| 78 | " | " | adipic | 3½ | 4.0 | 12.9 |
| 79 | " | " | citric | 3½ | 3.8 | 14.7 |
| 80 | " | glyoxylic | oxalic | 3½ | 3.4 | 15.8 |
| 81 | " | " | adipic | 3½ | 3.75 | 4.2 |
| 82 | " | " | citric | 3½ | 3.8 | 4.8 |
| 83 | " | levulnic | oxalic | 3½ | 3.35 | 5.2 |
| 84 | " | " | adipic | 3½ | 4.1 | — |

EXAMPLE 85

Dioxime (3.9 g), water (25 ml) and concentrated hydrochloric acid (15 ml) were stirred whilst a solution of sodium nitrite (10.35 g) in water (15 ml) was slowly added at between −20° C. and −5° C. The addition took 0.5 hour. The solution was allowed to warm to ambient temperature (20° C.). Urea was added to destroy the excess nitrite. Upon heating a small sample, pyrogallol was shown to be present by TLC.

EXAMPLE 86

To a suspension of calcium oxide (2.24 g) in water (100 ml) was passed sulphur dioxide until almost all the solid had dissolved. The clear supernatant liquor was decanted. To the decanted liquor was added dioxime (2.5 g). Sulphur dioxide was then passed for 3 hours while stirring at ambient temperature (20° C.). The mixture was then filtered. Upon acidification of the filtrate and boiling of a small sample, pyrogallol was shown to be present by TLC.

EXAMPLE 87

To a suspension of calcium oxide (2.24 g) in water (100 ml) was passed sulphur dioxide until almost all the solid had dissolved. The clear supernatant liquor was decanted and the liquor heated to 50° C. before dioxime (2.5 g) was added. Sulphur dioxide was passed through for 2 hours. A small sample of the solution was acidified and boiled; pyrogallol was shown to be present by TLC. The bulk of the solution was acidified to pH 1 with hydrochloric acid, and then refluxed for 0.5 hour. The resulting brown precipitate was filtered off. The pH of the filtrate was adjusted to 6 with 5 M sodium hydroxide solution, and the mixture then continuously extracted with ether. Evaporation of the ether gave 0.56 g of a brown oil, whose analysis showed a yield of 2.8% pyrogallol.

EXAMPLE 88

A slurry of calcium oxide (2.24 parts) in water (100 parts) was heated to 50° C. and sulphur dioxide bubbled through until a clear solution was obtained. Pyruvic acid (4.25 parts) and dioxime (2.5 parts) were added, and sulphur dioxide bubbled through at 50° C. for a further 4 hours. The reaction mixture was allowed to cool, and the solids filtered off. The pH of the filtrate was adjusted to 6.2 with 5 N NaOH and then continuously extracted with diethyl ether for 6 hours. The ether extract was dried over anhydrous sodium sulphate and evaporated under vacuum to yield a dark brown oil. The yield of pyrogallol assessed by gas chromatography was 18.9%.

I claim:

1. A process for preparing pyrogallol or a salt thereof, which process comprises deoximating at −20° to 200° C. cyclohexane-1,2,3-trione oxime or an oxime ester thereof or a salt of either, and recovering pyrogallol or a salt thereof, and when the deoximation is effected by hydrolysis, the amount of water employed in the hydrolysis is 0.2–1000 parts by weight per part by weight of the oxime, oxime ester thereof or salt of either.

2. A process according to claim 1 wherein pyrogallol itself is prepared.

3. A process according to claim 1 wherein the oxime itself is deoximated.

4. A process according to claim 1 wherein the oxime is cyclohexane-1,2,3-trione 1,3-dioxime.

5. A process according to claim 1 wherein the deoximation is effected by a process comprising hydrolysing the oxime, oxime ester or salt at −15° to 200° C., the amount of water employed in the hydrolysis being 0.2–1000 parts by weight per part by weight of the oxime, oxime ester or salt.

6. A process for preparing pyrogallol or a salt thereof, which process comprises deoximating cyclohexane-1,2,3-trione oxime or an oxime ester thereof or a salt of either by reacting the oxime, oxime ester or salt at −15° to 200° C. with bisulphite ion in the presence of water, and recovering pyrogallol or a salt thereof.

7. A process for preparing pyrogallol or a salt thereof, which process comprises deoximating cyclohexane-1,2,3-trione oxime or an oxime ester thereof or a salt of either by reacting the oxime, oxime ester or salt at −20° to 200° C. with aqueous nitrous acid, and recovering pyrogallol or a salt thereof.

8. A process for preparing pyrogallol, which process comprises hydrolysing cyclohexane-1,2,3-trione 1,3-dioxime at −15° to 200° C., the amount of water employed in the hydrolysis being 0.2–1000 parts by weight per part by weight of the dioxime, and recovering pyrogallol or a salt thereof.

9. A process according to claim 5 or 8 wherein the hydrolysis is conducted at a pH from −1 to 6.

10. A process according to claim 5 or 8 wherein the hydrolysis is conducted in the presence of an aldehydo-acid or a keto-acid.

11. A process according to claim 10 wherein the aldehydo-acid or keto-acid is pyruvic acid.

12. A process according to claim 9 wherein the hydrolysis is conducted in the presence of a secondary or tertiary amine.

13. A process according to claim 12 wherein the amine is morpholine, N-methylaniline or N,N-dimethylaniline.

14. A process according to claim 12 wherein the hydrolysis is conducted in the presence of hydrochloric acid.

15. A process according to claim 12 wherein the hydrolysis is conducted in the presence of a dicarboxylic acid.

16. A process according to claim 15 wherein the dicarboxylic acid is oxalic acid.

17. A process according to claim 5 or 8 wherein the hydrolysis is conducted at a temperature from 20° to 120° C.

18. A process according to claim 9 wherein the hydrolysis is conducted in the presence of an aldehydo-acid or a keto-acid.

19. A process according to claim 18 wherein the aldehydo-acid or keto-acid is pyruvic acid.

20. A process according to claim 13 wherein the hydrolysis is conducted in the presence of hydrochloric acid.

21. A process according to claim 13 wherein the hydrolysis is conducted in the presence of a dicarboxylic acid.

22. A process according to claim 21 wherein the dicarboxylic acid is oxalic acid.

23. A process according to claim 5 or 8 wherein the hydrolysis is conducted at a pH above 1, up to 6.

24. A process according to claim 5 or 8 wherein the hydrolysis is conducted at 40°–140° C.

25. A process according to claim 5 or 8 wherein the hydrolysis is conducted at a pH below 7 and in the presence of an organic acid.

* * * * *